US008760507B2

(12) United States Patent
Boehnlein et al.

(10) Patent No.: US 8,760,507 B2
(45) Date of Patent: Jun. 24, 2014

(54) LIGHT PIPE FOR IMAGING HEAD OF VIDEO INSPECTION DEVICE

(75) Inventors: Al Boehnlein, Ypsilanti, MI (US); Owen W. Draper, West Bloomfield, MI (US)

(73) Assignee: Inspectron, Inc., Novi, MI (US)

( * ) Notice: Subject to any disclaimer, the term of this patent is extended or adjusted under 35 U.S.C. 154(b) by 742 days.

(21) Appl. No.: 12/564,447

(22) Filed: Sep. 22, 2009

(65) Prior Publication Data

US 2010/0033563 A1    Feb. 11, 2010

Related U.S. Application Data

(63) Continuation-in-part of application No. 12/186,182, filed on Aug. 5, 2008.

(51) Int. Cl.
*H04N 9/47* (2006.01)

(52) U.S. Cl.
USPC ............................................ 348/84; 348/65

(58) Field of Classification Search
USPC ........................................... 348/65, 84
See application file for complete search history.

(56) References Cited

U.S. PATENT DOCUMENTS

| | | | |
|---|---|---|---|
| 3,748,483 A * | 7/1973 | Englund et al. ............... 250/566 |
| 4,469,398 A * | 9/1984 | De Baets et al. ............... 385/89 |
| 4,595,265 A | 6/1986 | Hodgson et al. |
| 4,805,984 A * | 2/1989 | Cobb, Jr. ....................... 385/133 |
| 5,373,317 A * | 12/1994 | Salvati et al. .................. 348/65 |
| 5,416,638 A * | 5/1995 | Broome ......................... 359/656 |
| 5,506,929 A | 4/1996 | Tai et al. |
| 5,527,261 A * | 6/1996 | Monroe et al. ................. 600/109 |
| 5,531,664 A | 7/1996 | Adachi et al. |
| 5,555,161 A | 9/1996 | Roe et al. |
| 5,633,675 A * | 5/1997 | Danna et al. ..................... 348/65 |
| 5,651,047 A | 7/1997 | Moorman et al. |
| 5,662,586 A * | 9/1997 | Monroe et al. ................. 600/110 |
| 5,668,913 A | 9/1997 | Tai et al. |
| 5,745,165 A * | 4/1998 | Atsuta et al. ..................... 348/65 |
| 5,879,288 A * | 3/1999 | Suzuki et al. ................. 600/176 |
| 5,880,826 A | 3/1999 | Jung et al. |
| 5,926,262 A | 7/1999 | Jung et al. |
| 5,986,746 A | 11/1999 | Metz et al. |

(Continued)

OTHER PUBLICATIONS

"Computer Modeling of LED Light Pipe Systems for Uniform Display Illumination" Solid State Lighting and Displays, Proceedings of SPIE. Copyright 2001. Society of Photo-Optical Instrumentation Engineers. John F. Van Derlofske, Lighting Research Center,Rensselaer Polytechnic Institute, Troy, NY 12180. 12 pages.

*Primary Examiner* — Backhean Tiv
(74) *Attorney, Agent, or Firm* — Brinks Gilson & Lione

(57) ABSTRACT

A light dispersal unit or light pipe for a video imaging device includes a transparent body. The body includes a tubular ring having an outer diameter and a through bore defining an inner diameter. Four equidistantly spaced raised portions are homogenously joined to the tubular ring. The ring has a semi-circular shape corresponding to the outer and inner diameters of the tubular ring. The raised portions each include a slot created between opposed first and second extending portions, the slot having an end wall and opposed first and second slot walls. A rounded end face defines a free end of each of the first and second extending portions facing away from the tubular ring. The rounded end face includes at least two curved portions each having a different radius of curvature. The light pipe can be a tapered light pipe having a flange portion for mounting the tapered light pipe.

23 Claims, 15 Drawing Sheets

(56) References Cited

U.S. PATENT DOCUMENTS

| | | | |
|---|---|---|---|
| 6,031,566 A | 2/2000 | Leo | |
| 6,091,453 A | 7/2000 | Coan et al. | |
| 6,106,457 A | 8/2000 | Perkins et al. | |
| 6,118,521 A | 9/2000 | Jung et al. | |
| 6,186,944 B1 | 2/2001 | Tsai | |
| 6,188,471 B1 | 2/2001 | Jung et al. | |
| 6,319,199 B1 | 11/2001 | Sheehan et al. | |
| 6,332,092 B1 | 12/2001 | Deckert et al. | |
| 6,361,489 B1 | 3/2002 | Tsai | |
| 6,373,573 B1 | 4/2002 | Jung et al. | |
| 6,379,011 B1 | 4/2002 | Knox | |
| 6,394,355 B1 | 5/2002 | Schlieffers et al. | |
| 6,428,198 B1 | 8/2002 | Saccomanno et al. | |
| 6,476,970 B1 | 11/2002 | Smith | |
| 6,478,730 B1 | 11/2002 | Bala et al. | |
| 6,484,050 B1 | 11/2002 | Carroll et al. | |
| 6,487,440 B2 | 11/2002 | Deckert et al. | |
| 6,504,985 B2 | 1/2003 | Parker et al. | |
| 6,603,874 B1 | 8/2003 | Stern et al. | |
| 6,619,820 B2 | 9/2003 | Li | |
| 6,626,825 B2 | 9/2003 | Tsai | |
| 6,686,950 B1 * | 2/2004 | Caffon et al. | 348/83 |
| 6,695,775 B2 * | 2/2004 | Watanabe et al. | 600/176 |
| 6,819,506 B1 * | 11/2004 | Taylor et al. | 359/726 |
| 6,829,098 B2 | 12/2004 | Smith | |
| 6,831,679 B1 * | 12/2004 | Olsson et al. | 348/84 |
| 6,840,623 B2 | 1/2005 | Li | |
| 6,855,106 B2 * | 2/2005 | May et al. | 600/112 |
| 6,863,651 B2 | 3/2005 | Remijan et al. | |
| 6,869,206 B2 | 3/2005 | Zimmerman et al. | |
| 6,880,402 B1 | 4/2005 | Couet et al. | |
| 6,886,406 B1 | 5/2005 | Couet et al. | |
| 6,896,653 B1 | 5/2005 | Vail, III et al. | |
| 6,898,353 B2 | 5/2005 | Li | |
| 6,926,435 B2 | 8/2005 | Li | |
| 6,931,149 B2 | 8/2005 | Hagene et al. | |
| 6,939,009 B2 | 9/2005 | Fischer et al. | |
| 6,953,432 B2 * | 10/2005 | Schiefer | 600/175 |
| 6,957,905 B1 | 10/2005 | Pritchard et al. | |
| 7,050,245 B2 * | 5/2006 | Tesar et al. | 359/771 |
| 7,054,076 B2 * | 5/2006 | Tesar et al. | 359/726 |
| 7,137,948 B2 | 11/2006 | Tsai | |
| 7,151,874 B2 | 12/2006 | Li | |
| 7,153,015 B2 | 12/2006 | Brukilacchio | |
| 7,172,290 B2 | 2/2007 | Li | |
| 7,178,941 B2 | 2/2007 | Roberge et al. | |
| 7,209,624 B2 * | 4/2007 | Reynolds et al. | 385/133 |
| 7,232,228 B2 | 6/2007 | Li | |
| 7,261,438 B2 * | 8/2007 | Alessio | 362/268 |
| 7,261,453 B2 | 8/2007 | Morejon et al. | |
| 7,306,352 B2 | 12/2007 | Sokolov | |
| 7,306,559 B2 | 12/2007 | Williams | |
| 7,314,279 B2 | 1/2008 | Teijido et al. | |
| 7,317,506 B2 | 1/2008 | Flagello et al. | |
| 7,333,083 B1 | 2/2008 | Theytaz et al. | |
| 7,338,187 B2 | 3/2008 | Li | |
| 7,339,735 B2 | 3/2008 | Li | |
| 7,350,928 B2 * | 4/2008 | Liao et al. | 353/81 |
| 7,357,518 B2 * | 4/2008 | Iinuma | 353/101 |
| 7,360,905 B2 | 4/2008 | Davis et al. | |
| 7,410,283 B2 * | 8/2008 | West et al. | 362/573 |
| 7,413,543 B2 * | 8/2008 | Banik et al. | 600/129 |
| 7,419,467 B2 | 9/2008 | Tsai | |
| 7,424,197 B2 | 9/2008 | Winston et al. | |
| 7,445,340 B2 | 11/2008 | Conner et al. | |
| 7,451,917 B2 | 11/2008 | McCall et al. | |
| 7,452,086 B2 | 11/2008 | Li | |
| 7,488,101 B2 | 2/2009 | Brukilacchio | |
| 7,874,714 B2 * | 1/2011 | Yoneda et al. | 362/555 |
| 7,885,010 B1 * | 2/2011 | Bodor et al. | 359/660 |
| 7,962,023 B2 * | 6/2011 | Lee et al. | 396/55 |
| 8,118,733 B2 * | 2/2012 | Scott et al. | 600/130 |
| 2001/0000672 A1 * | 5/2001 | Ooshima et al. | 348/65 |
| 2002/0033931 A1 | 3/2002 | Knox | |
| 2002/0154510 A1 | 10/2002 | Li | |
| 2003/0063261 A1 | 4/2003 | Li | |
| 2003/0128341 A1 | 7/2003 | Li | |
| 2003/0215127 A1 | 11/2003 | Stern et al. | |
| 2004/0233655 A1 | 11/2004 | Zimmerman et al. | |
| 2005/0063196 A1 | 3/2005 | Li | |
| 2005/0073653 A1 | 4/2005 | Li | |
| 2005/0129108 A1 * | 6/2005 | Bendall et al. | 375/240.01 |
| 2005/0213046 A1 | 9/2005 | Teijido et al. | |
| 2005/0218537 A1 * | 10/2005 | Cok et al. | 264/1.24 |
| 2006/0061870 A1 | 3/2006 | Wang | |
| 2006/0132910 A1 | 6/2006 | Defever et al. | |
| 2006/0133732 A1 | 6/2006 | Li | |
| 2006/0281772 A1 * | 12/2006 | Baindur et al. | 514/266.22 |
| 2006/0290899 A1 | 12/2006 | Davis et al. | |
| 2007/0208312 A1 * | 9/2007 | Norton et al. | 604/284 |
| 2007/0258049 A1 | 11/2007 | Shaoulov et al. | |
| 2007/0263298 A1 | 11/2007 | El-Ghoroury et al. | |
| 2007/0291491 A1 | 12/2007 | Li et al. | |
| 2007/0291505 A1 | 12/2007 | Fortenberry et al. | |
| 2008/0018861 A1 | 1/2008 | Schuck et al. | |
| 2008/0018999 A1 | 1/2008 | Schuck et al. | |
| 2008/0030974 A1 | 2/2008 | Abu-Ageel | |
| 2008/0123343 A1 | 5/2008 | Kobayashi et al. | |
| 2008/0174868 A1 | 7/2008 | Schuck et al. | |
| 2009/0040465 A1 | 2/2009 | Conner et al. | |
| 2009/0046150 A1 * | 2/2009 | Hayakawa et al. | 348/148 |
| 2009/0109283 A1 * | 4/2009 | Scott et al. | 348/65 |

* cited by examiner

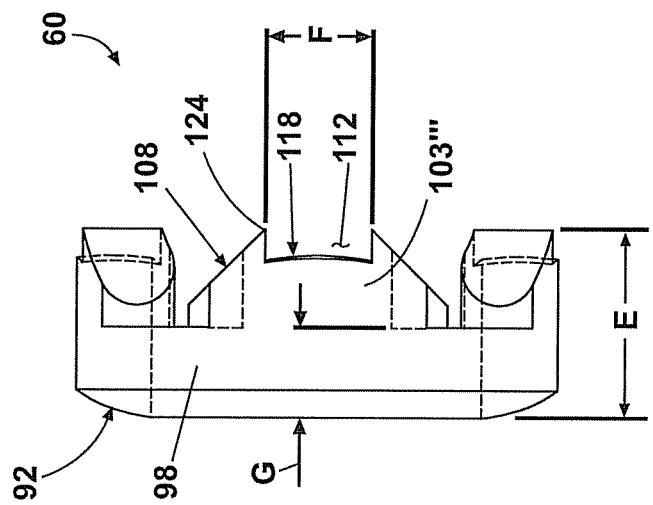
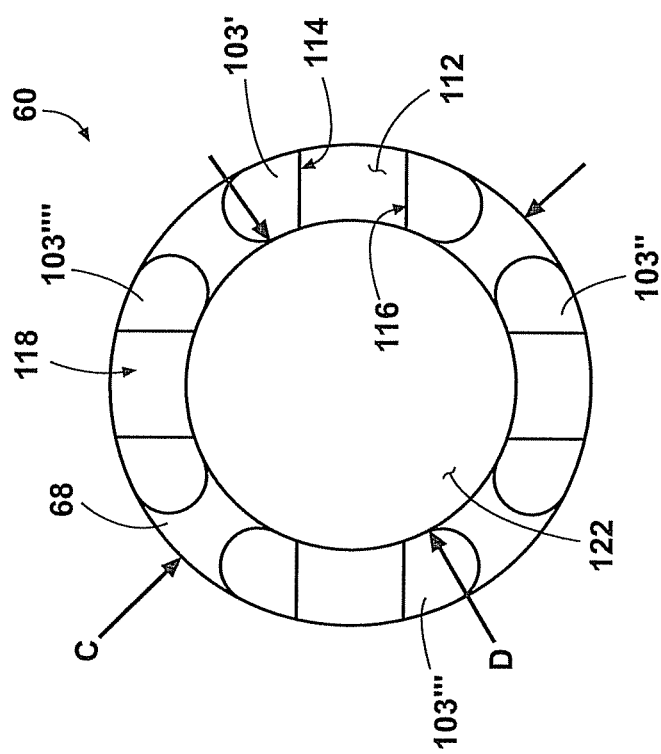

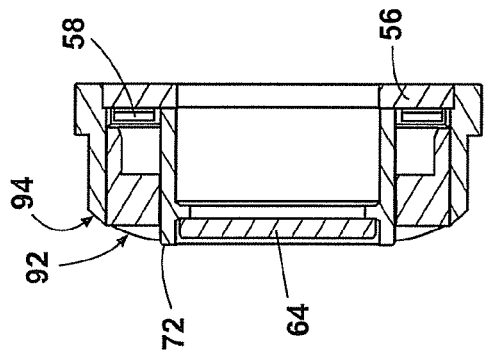
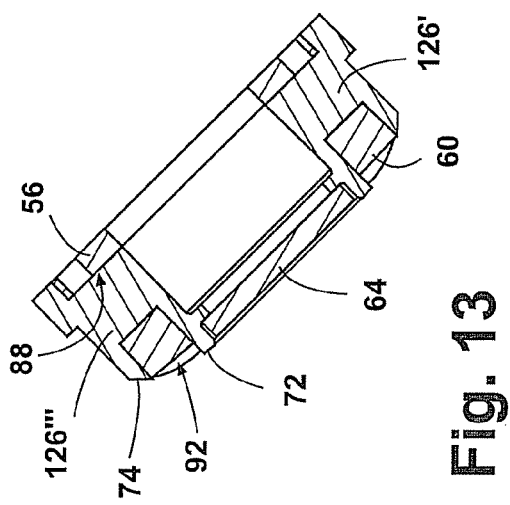
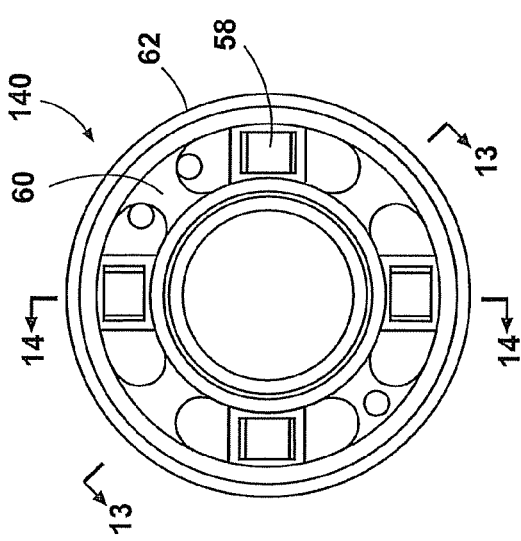

LIGHT PIPE FOR IMAGING HEAD OF VIDEO INSPECTION DEVICE

CROSS-REFERENCE TO RELATED APPLICATIONS

This application is a continuation-in-part of U.S. patent application Ser. No. 12/186,182 filed on Aug. 5, 2008. The entire disclosure of the above application is incorporated herein by reference.

FIELD

The present disclosure relates to borescopes and video scopes.

BACKGROUND

The statements in this section merely provide background information related to the present disclosure and may not constitute prior art.

Borescopes and video scopes used for inspecting visually obscure locations, hereinafter referred to as remote inspection devices, are typically tailored for particular applications. For instance, some remote inspection devices have been tailored for use by plumbers to inspect pipes and drains. Likewise, other types of remote inspection devices have been tailored for use by mechanics to inspect interior compartments of machinery being repaired.

Analog remote inspection devices are known which have hand-held control units using a power source such as a plurality of batteries, with data leads and power lines extending through a flexible cable to a light diffusing/image receiving head. Such devices commonly provide a remote light source to illuminate the area of interest and an imaging device to capture the illuminated image. Images provided by analog signal devices are adequate for many applications, however, where fine image detail is desired digital signal devices can convey greater volumes of data to improve the resolution. To further improve resolution, an increased power light source can also be used, created for example by increasing a quantity of light emitting components. However, increasing the quantity of light emitting components can introduce focal distortion and/or areas where light is not evenly diffused to illuminate a desired object.

SUMMARY

According to several embodiments of the present disclosure, a light dispersal unit for a video imaging device includes a transparent body having a tubular ring and at least one raised portion homogenously joined to the tubular ring. The at least one raised portion includes a slot created between opposed first and second extending portions having an end wall and opposed first and second slot walls. A rounded end face defining a free end of each of the first and second extending portions faces away from the tubular ring.

According to other embodiments, a light dispersal unit or light pipe for a video imaging device includes a transparent body. The body includes a tubular ring having an outer diameter and a through bore defining an inner diameter. Four equidistantly spaced raised portions are homogenously joined to the tubular ring. The ring has a semi-circular shape corresponding to the outer and inner diameters of the tubular ring. The raised portions each include a slot created between opposed first and second extending portions, the slot having an end wall and opposed first and second slot walls. A rounded end face defines a free end of each of the first and second extending portions facing away from the tubular ring. The rounded end face includes at least two curved portions each having a different radius of curvature.

According to still other embodiments, a video imaging device includes a circuit board having a light emitting diode connected to the circuit board. A transparent light pipe has a tubular ring and at least one raised portion homogenously joined to the tubular ring. The at least one raised portion includes a slot created between opposed first and second extending portions having an end wall and opposed first and second slot walls. A rounded end face defining a free end of each of the first and second extending portions faces away from the tubular ring. A light pipe cap adapted to retain the circuit board and the light pipe having the slot of the light pipe aligned with the light emitting diode so that light emitted by the light emitting diode is received at the slot and by the rounded end face of each of the first and second extending portions.

According to further embodiments, a video imaging device, includes a circuit board having four light emitting diodes connected to the circuit board equidistantly spaced from each other. A transparent light pipe includes a tubular ring having an outer diameter and a through bore defining an inner diameter. Four equidistantly spaced raised portions are homogenously joined to the tubular ring and have a semi-circular shape corresponding to the outer and inner diameters of the tubular ring. The raised portions each include a slot created between opposed first and second extending portions having an end wall and opposed first and second slot walls. A rounded end face defines a free end of each of the first and second extending portions facing away from the tubular ring. The rounded end face includes at least two curved portions each having a different radius of curvature. A light pipe cap adapted to retain the circuit board and the light pipe in a manner which has each slot of the light pipe aligned with one of the light emitting diodes so that light emitted by each light emitting diode is received at the slot and by the rounded end face of each of the first and second extending portions.

According to further embodiments, a tapered light pipe for a video imaging device includes a body including a first end defining a minimum body diameter oppositely positioned with respect to a second end defining a maximum body diameter; and a conical shaped perimeter wall extending between the first and second ends. A flange portion integrally is connected to the body at the body second end and extends transversely with respect to a longitudinal axis of the light pipe, a flange diameter of the flange portion being greater than the maximum body diameter.

According to further embodiments, an imager assembly for a video imaging device includes a tapered light pipe including a conical shaped body including a first end having a minimum body diameter and an oppositely positioned second end having a maximum body diameter; a flange portion integrally connected to the body second end and extending transversely with respect to a longitudinal axis of the tapered light pipe, a flange diameter of the flange portion being greater than the maximum body diameter; and a convex curved surface axially extending from the flange portion and oppositely directed with respect to the body. An imager end cap having a light pipe mounting cavity includes a counterbore seating surface. A flange mount surface of the flange portion is oriented transverse to the longitudinal axis. The flange mount surface contacts the counterbore seating surface in a seated position of the tapered light pipe. Contact between the flange mount surface and the counterbore seating surface is the only portion of the tapered light pipe in contact with the imager assembly.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 7 is a bottom plan view of the light pipe of FIG. 6;

FIG. 8 is a side elevational view of the light pipe of FIG. 6;

FIG. 12 is a top plan view of a cap/circuit board assembly of the present disclosure;

FIG. 13 is a cross sectional elevational view taken at section 13 of FIG. 12;

FIG. 14 is a cross sectional elevational view taken at section 14 of FIG. 12;

DETAILED DESCRIPTION

Figure 1:
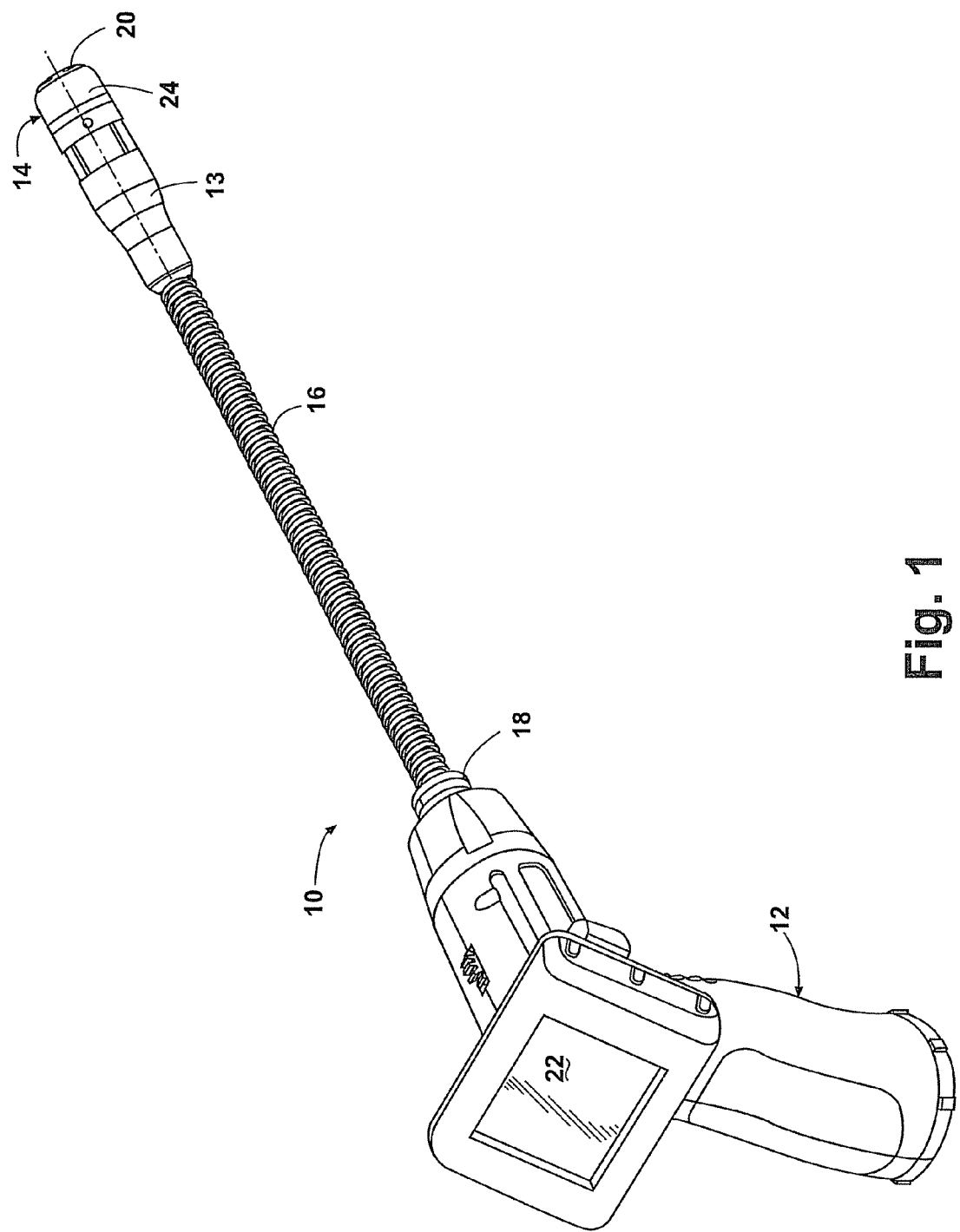
FIG. 1 is a perspective view of an imager assembly for remote inspection devices of the present disclosure.

The following description is merely exemplary in nature and is not intended to limit the present disclosure, application, or uses. It should be understood that throughout the drawings, corresponding reference numerals indicate like or corresponding parts and features.

Referring to FIG. 1, a remote inspection device 10 can include a hand-held display housing 12 and an imager assembly 13 including an imager head sub-assembly 14, a flexible tube 16 allowing imager head sub-assembly 14 to be remotely and movably displaced with respect to display housing 12, and a housing connection sub-assembly 18 releasably connecting flexible tube 16 to display housing 12. Imager head sub-assembly 14 includes an image receiving end 20 adapted to receive and digitally send a viewed image from imager head sub-assembly 14 to an image view screen 22 provided with display housing 12. The image view screen 22 is adapted to present an image transferred by the imager head sub-assembly as a digital signal. An imager end cap 24 is provided to releasably engage the image receiving end 20 to imager assembly 13.

Figure 2:
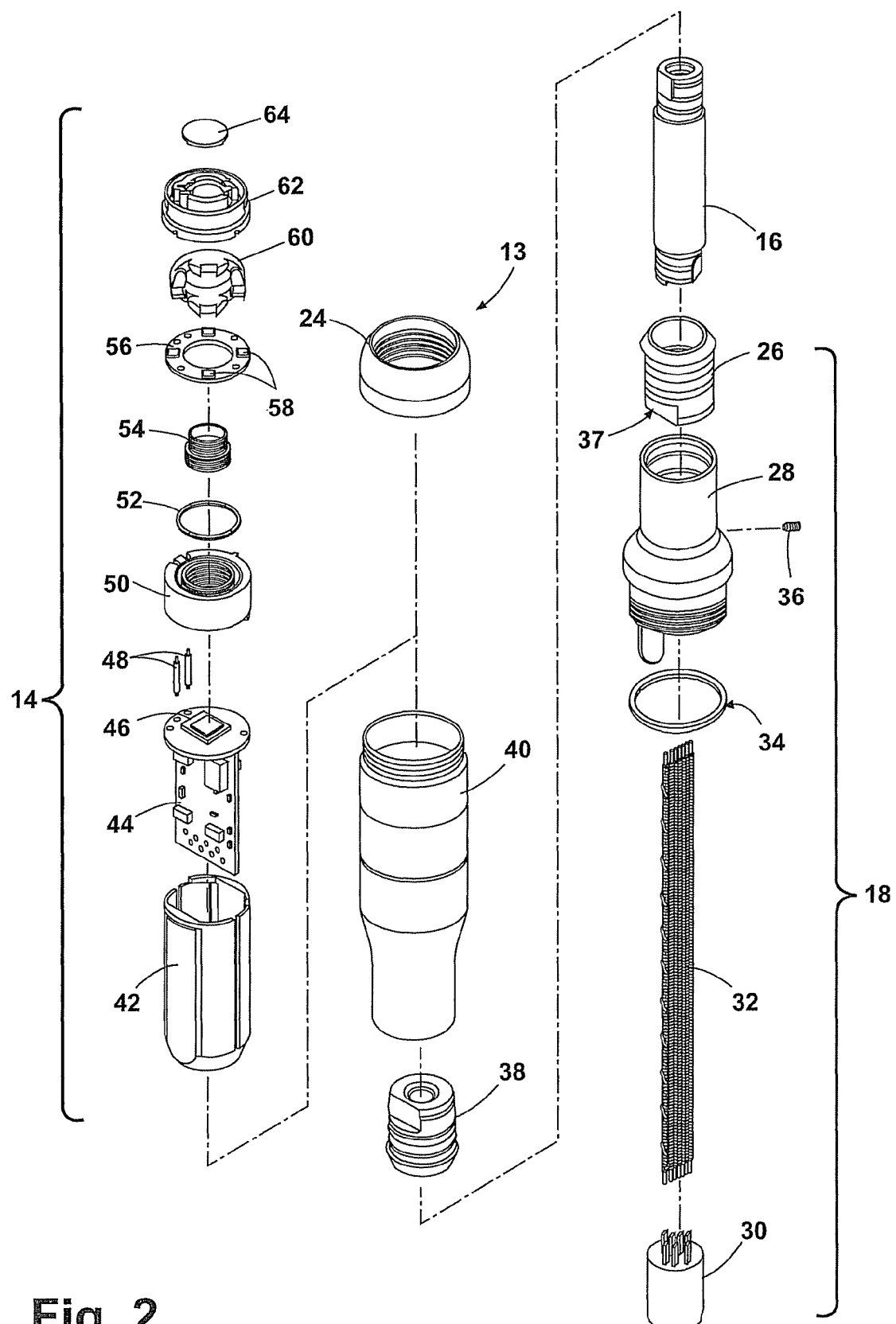
FIG. 2 is an assembly view of the component parts of the imager head sub-assembly of FIG. 1.

Referring to FIG. 2, housing connection sub-assembly 18 includes a first ferrule 26 which is slidably received and pressed into frictional engagement with a male connector 28. A multiple pin electrical connector 30 is provided which includes a plurality of pins which provide connection points for the multiple individual wires of a wiring harness 32 which is received through each of first ferrule 26 and male connector 28. A seal 34 such as an elastic O-ring is also provided to act as an environmental seal member between male connector 28 and display housing 12 (shown in FIG. 1). A fastener 36 such as a set screw is also provided to frictionally engage the multiple pin electrical connector 30 within male connector 28.

Wiring harness 32 provides multiple wires which pass through first ferrule 26 into a longitudinal cavity of flexible tube 16 and exit through a second ferrule 38 which is press fit into an imager body 40. Imager assembly 13 includes imager head sub-assembly 14 which is retained by imager end cap 24 threadably engaged to imager body 40. Imager head sub-assembly 14 includes second ferrule 38, imager body 40 and each of a circuit board retainer 42, a circuit board assembly 44 having an imager device 46 fixed thereto, a plurality of electrically conductive pins 48, a lens receiving unit 50, a gasket seal 52 such as an O-ring, a lens assembly 54, and a light source circuit board 56 having at least one and in at least one embodiment four (4) high intensity light emitting diodes (LEDs) 58 equidistantly spaced from each other in a circular pattern. A molded light dispersal unit or light pipe unit 60 is positioned proximate to (above as shown in FIG. 2) circuit board 56 to receive and diffuse light transmitted by LEDs 58. Light pipe unit 60 is held within a light pipe cap 62, which is also adapted to hold a sapphire window 64 which receives reflected light for focusing using a lens of lens assembly 54 onto imager device 46. Imager end cap 24 is threadably received on a free end of imager body 40 after the components of imager head sub-assembly 14 are installed. Wiring connections are also made between the individual wires of wiring harness 32 and circuit board assembly 44.

High intensity light emitting diodes (LEDs) 58 produce light from energy received through circuit board 56 to illuminate an area in a viewing range of lens assembly 54 and imager device 46. The illuminated image received by imager device 46 can be converted via circuit board assembly 44 to a digital signal and transferred via wiring harness 32 to the image view screen 22 of display housing 12 shown in FIG. 1. According to other embodiments, the illuminated image can also be converted to an analog signal.

Figure 3:
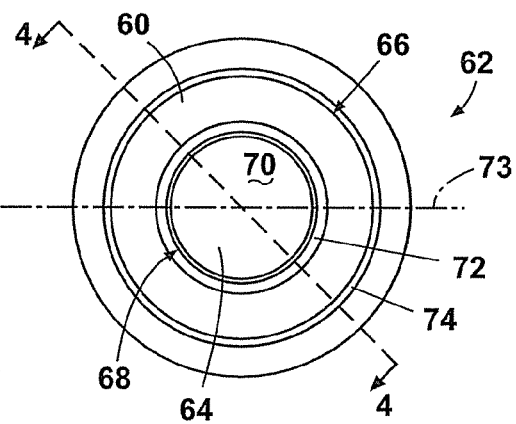
FIG. 3 is a top plan view of an imager head having a light pipe, cap, and nut of the present disclosure.

Referring to FIG. 3, sapphire window 64 can be centrally positioned within an interior wall defined by light pipe cap 62. Light pipe unit 60 is received in a circular shelf 66 formed in light pipe cap 62. Sapphire window 64 is supported in a counterbore 68 extending into a bore 70 of light pipe cap 62. Shelf 66 is defined between an inner wall 72 and an outer wall 74. Light is therefore transmitted throughout the donut or toroid shape of light pipe unit 60 and the reflected (image containing) light is received through sapphire window 64.

Figure 4:
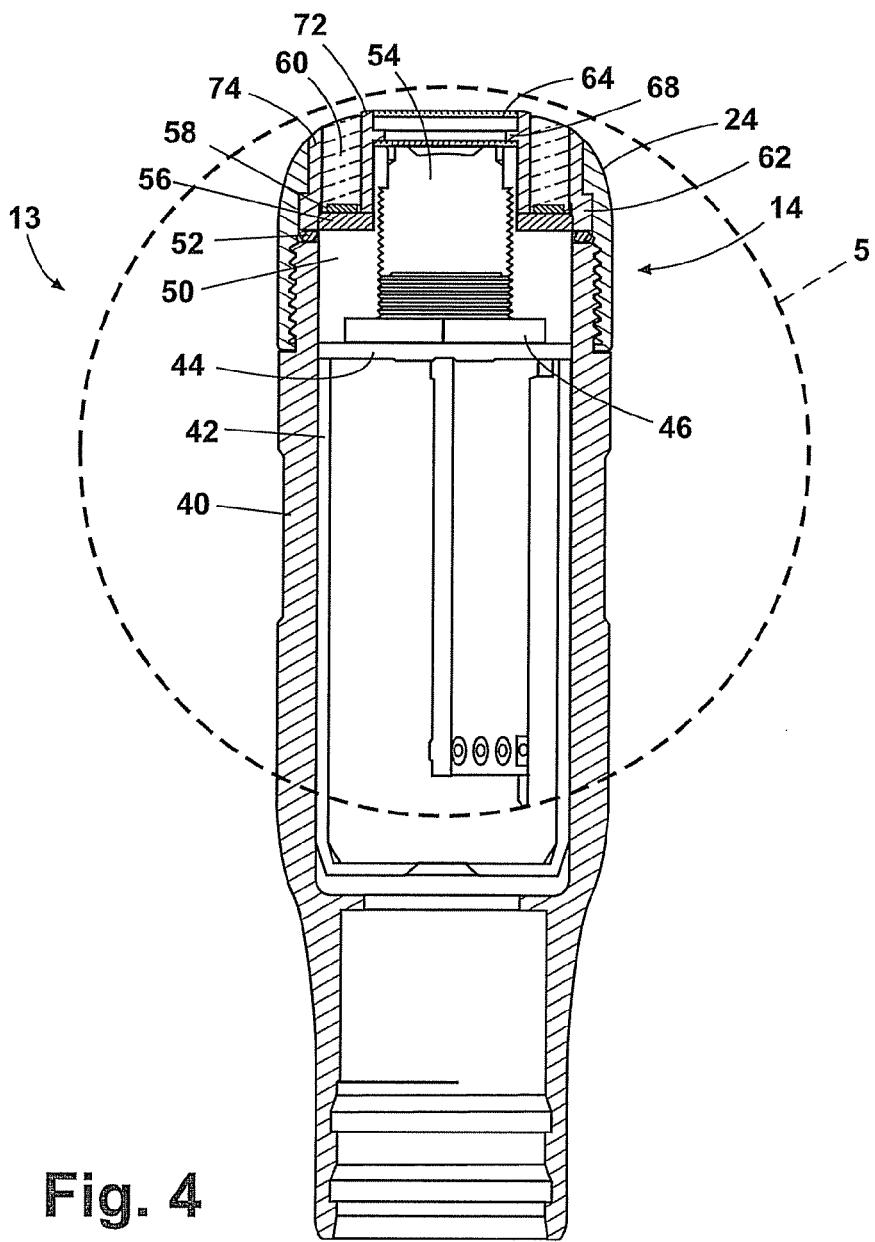
FIG. 4 is cross sectional front elevational view taken at section 4 of FIG. 3.

Referring to FIG. 4, an imager head sub-assembly 14 according to several embodiments provides a configuration having lens assembly 54 threadably engaged within lens receiving unit 50. Lens receiving unit 50 provides support for circuit board 56. Circuit board 56 in turn provides support for inner wall 72 of light pipe cap 62, while an interface between outer wall 74 of light pipe cap 62 and imager body 40 is sealed using gasket seal 52. As shown, the LEDs 58 are aligned on circuit board 56 to transmit light generated by the LEDs 58 through the body of light pipe unit 60 as light rays "B" shown in FIG. 5. Light transmitted by LEDs 58 and reflected by an object (not shown) and received through sapphire window 64 is digitally transmissible through lens assembly 54 using imager device 46 to circuit board assembly 44, which is retained at least partially within circuit board retainer 42.

Figure 5:
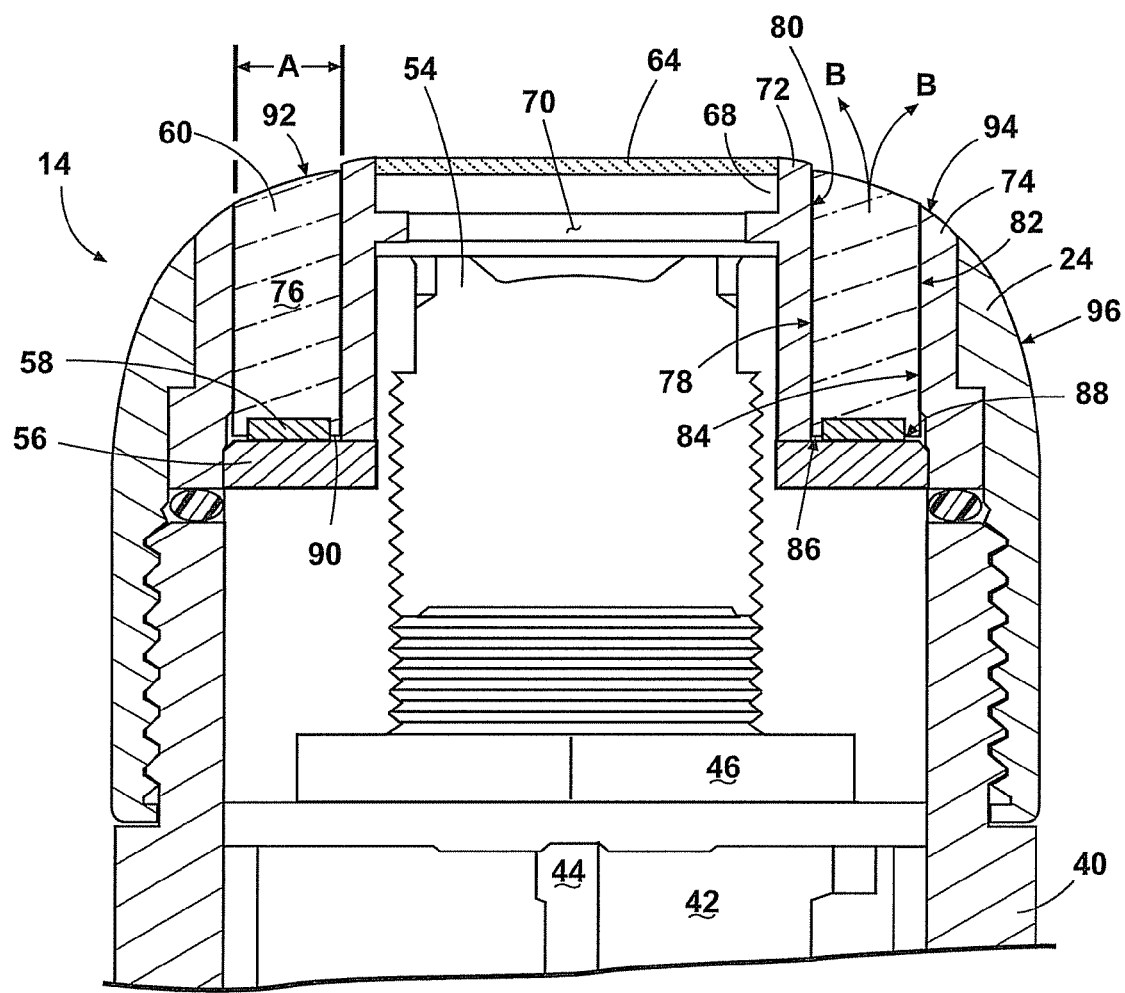
FIG. 5 is a cross sectional front elevational view of area 5 of FIG. 4.

Referring to FIG. 5, light pipe unit 60 includes a toroidal wall 76 which is received in shelf 66 of light pipe cap 62. Toroidal wall 76 has a dimensionally controlled width "A" which promotes contact between a first face 78 to an outward facing surface 80 of inner wall 72, and a second face 82 to an inward facing surface 84 of outer wall 74. Contact is maintained for first and second faces 78, 82 to minimize moisture/dirt intrusion. According to several embodiments contact made by first and second faces 78, 82 eliminates the need for a sealant or adhesive at these locations. An end face 86 of individual sections of toroidal wall 76 contacts an upper surface 88 of circuit board 56, and according to several embodiments a sealant layer 90 such as a silicone is applied at the interface between end faces 86 and upper surface 88. Toroidal wall 76 has a curved upper surface 92 whose geometry is adapted to closely match a curvature of an outer surface 94 of outer wall 74 which is also adapted to closely match a curvature of an outward facing surface 96 of imager end cap 24.

Referring to FIG. 6 and again to FIG. 5, light pipe unit 60 can be molded or formed from a polymeric material to create a tubular ring 98 having first and second opposed surfaces 100, 102. A plurality of raised portions 103 are created to match a quantity of LEDs 58. Each raised portion 103 includes first and second extending portions 104, 106, individually having a first and second curved end surface 108, 110 defining a free end of the first and second extending portions 104, 106 respectively. A slot 112 is created in each raised portion 103 adapted to allow one of the LEDs 58 to be received within the slot 112. Each slot 112 is defined by opposed first and second slot walls 114, 116, and a slot end wall 118. Each of the first and second extending portions 104, 106 can have a rounded end 120 which extends from second surface 102 to intersect either curved end surface 108 or 110. Light generated by each LED 58 enters the raised portion 103 through opposed slot walls 114, 116, and slot end wall 118. The geometry of curved end surfaces 108, 110 is adapted to maximize diffusion/transmission of light through raised portions 103 and tubular ring 98.

According to several embodiments, light pipe unit 60 can be constructed using a molding process such as injection or insert molding from a polymeric material to create a transparent body having tubular-shaped ring 98 and at least one raised portion 103 homogenously joined to the tubular ring 98. The at least one raised portion 103 includes a slot 112 created between opposed first and second extending portions 104, 106 having an end wall 118 and opposed first and second slot walls 114, 116 which can be oriented perpendicular to end wall 118. The rounded end face 108, 110 defines a free end of each of the first and second extending portions 104, 106 and face away from, or outward with respect to the tubular ring 98.

Referring to FIGS. 7 and 8, and again to FIG. 5, according to several embodiments, four (4) raised portions 103, identified as raised portions 103', 103", 103''', and 103'''' are provided, corresponding to a quantity of four (4) LEDs 58. The four raised portions 103 each have their slots 112 equidistantly spaced from the slots 112 of proximate raised portions 103 (e.g., in the exemplary embodiment shown spaced at 90 degree increments). According to several embodiments, tubular ring 68 of light pipe unit 60 can have an outer diameter "C" and an inner diameter "D" defined by a through bore 122, and a total height "E". According to several embodiments, outer diameter "C" can have a range of approximately 12.6 mm to 12.7 mm, inner diameter "D" can have a range of approximately 8.7 mm to 8.8 mm, and total height "E" can have a range of approximately 4.88 mm to 4.98 mm. Each slot 112 can have a width "F" having a range of approximately 2.81 mm to 2.91 mm, and tubular ring 98 can have a thickness "G" having a range of approximately 2.28 mm to 2.38 mm. The dimensions give herein are exemplary only and can vary at the discretion of the manufacturer.

Curved end surfaces 108, 110 can define a convex shaped surface have a radius of curvature. Slot end walls 118 can be substantially flat or according to several embodiments can define a convex shape facing away from tubular ring 98 having a radius of curvature. An apex 124 is created at the junction of either slot wall 114 or slot wall 116 with curved end surface 108 or 110, respectively, which can define a sharp corner adapted to minimize the surface area of light pipe unit 60 in contact with circuit board 56 and to maximize the surface areas of first and second curved end surfaces 108, 110 which receive and therefore diffuse light radially transmitted from LEDs 58 or reflected from upper surface 88 of circuit board 56.

Figure 9:
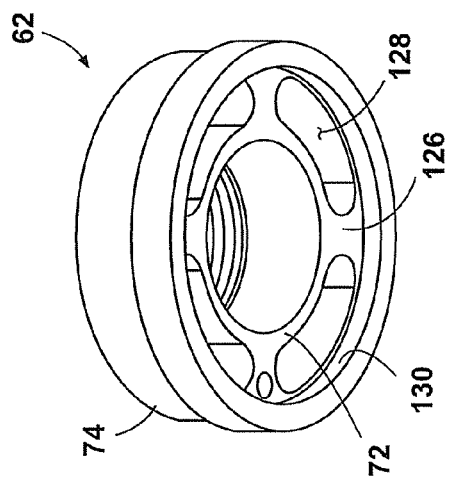
FIG. 9 is bottom perspective view of a light pipe cap of the present disclosure.

Referring to FIG. 9, an under or lower surface of light pipe cap 62 provides a plurality of lands 126 which structurally join the inner wall 72 to the outer wall 74. A plurality of curved bores 128 are provided between each of the lands 126. Curved bores 128 are provided to receive individual ones of the raised portions 103 of the light pipe unit 60. The geometry of curved bores 128 therefore closely matches the geometry of the individual raised portions 103 of the light pipe unit 60 so that a sealant is not required to be inserted between the individual raised portions 103 and the walls defined by the curved bores 128. An inner flange wall 130 is also created which has a diameter substantially matching that of an outer diameter of the light source circuit board 56 shown in reference to FIG. 5 when light pipe cap 62 is assembled together with light source circuit board 56.

Figure 10:
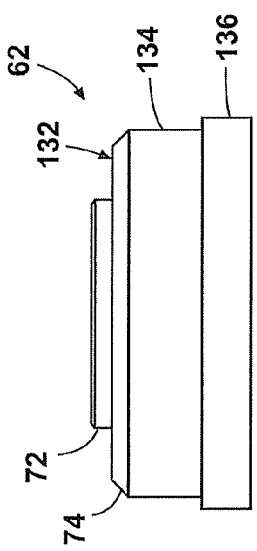
FIG. 10 is a front elevational view of the light pipe cap of FIG. 9.

Referring to FIG. 10, light pipe cap 62 further defines a wall end face 132 from which inner wall 72 extends beyond. A wall perimeter surface 134 is provided for outer wall 74. A flange surface 136 is provided as an outward facing surface opposed to inner flange wall 130 shown in FIG. 9.

Figure 11:
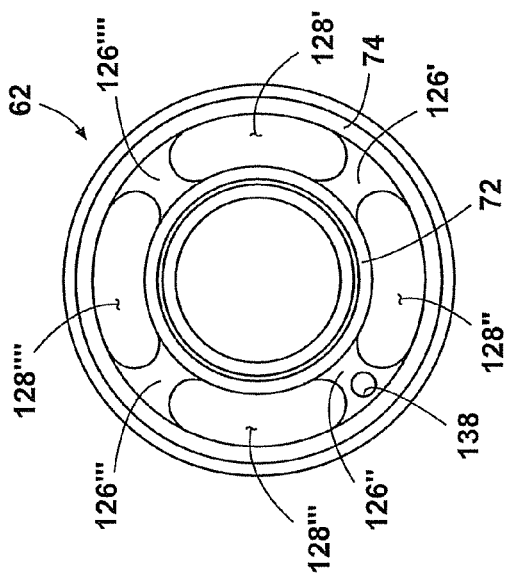
FIG. 11 is a bottom plan view of the light pipe cap of FIG. 9.

Referring to FIG. 11, according to several embodiments light pipe cap 62 is adapted to provided for lands 126 shown as land 126', 126", 126''' and 126''''. A quantity of four bores 128 is also provided shown as curved bores 128', 128", 128''', and 128''''. Each of the curved bores 128 and the lands 126 are equidistantly spaced from each other. According to additional embodiments, at least one and in several embodiments a plurality of clearance apertures 138 can be provided in individual ones of the lands 126. In the examples shown, a single clearance aperture 138 is provided in lands 126". Clearance apertures 138 are provided to receive an alignment pin (not shown) to rotationally orient the light pipe cap 62. Clearance apertures 138 can also be used for passage of electrical wires if necessary.

Referring to FIG. 12, a cap/circuit board assembly 140 shows an exemplary orientation of light pipe cap 62 with respect to the plurality of LEDs 58. Each of the LEDs 58 are oriented to centrally align with individual ones of the curved bores 128 of light pipe cap 62.

Referring to FIG. 13 and again to FIG. 9, the light pipe unit 60 is shown assembled into light pipe cap 62 together with sapphire window 64. Light source circuit board 56 is also shown positioned within the inner flange wall 130 defined by light pipe cap 62. Each of the curved upper surfaces 92 of light pipe cap 62 are shown positioned between the inner and outer walls 72, 74 of light pipe cap 62. The upper surface 88 of light source circuit board 56 abuts individual ones of the lands 126 in the assembled position of light source circuit board 56.

Figure 6:
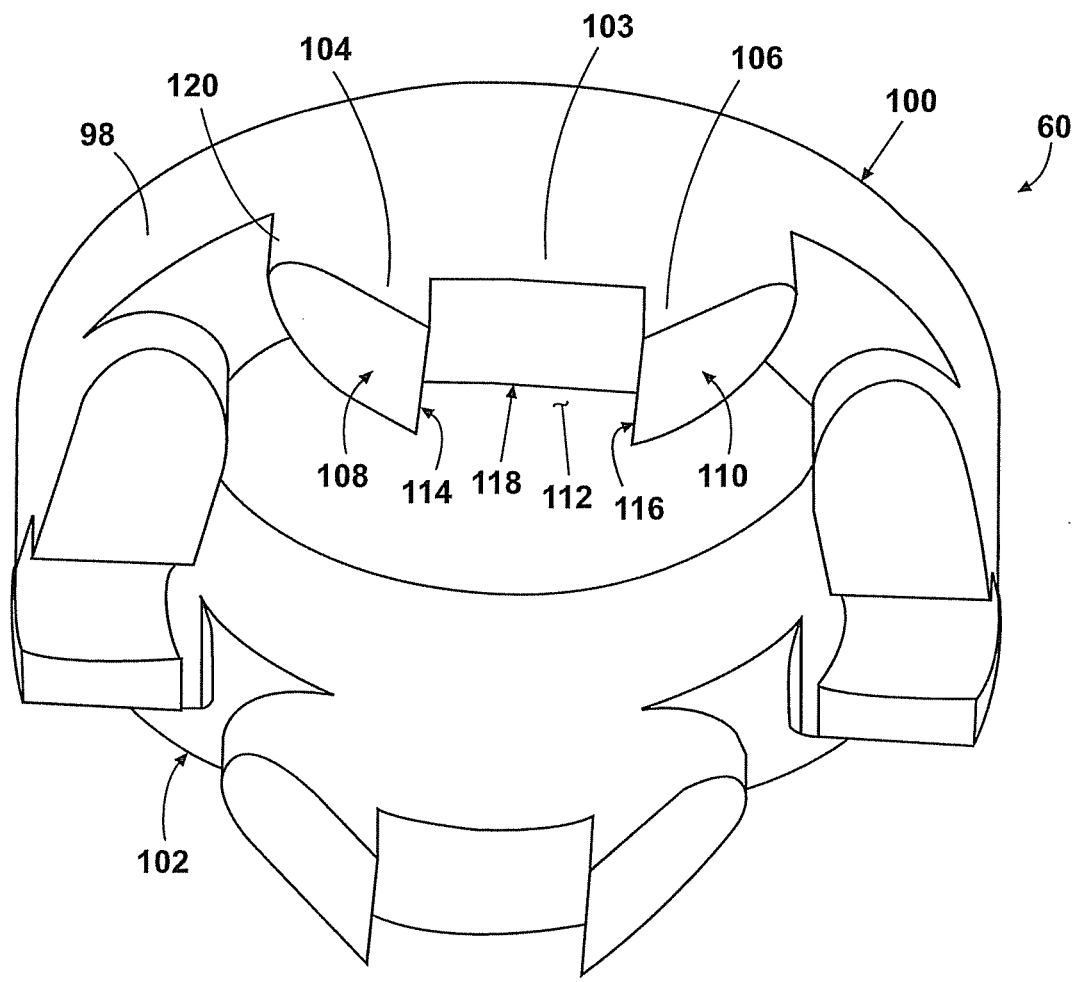
FIG. 6 is a bottom perspective view of a light pipe of the present disclosure.

Referring to FIG. 14 and again to FIGS. 6-8, individual ones of the LEDs 58 are shown in their aligned positions between inner wall 72 and outer wall 74 so that light generated by the LEDs 58 can be transmitted through light pipe unit 60 through curved upper surfaces 92. Each of the raised portions 103 of the transparent light pipe unit 60 further includes a first apex 124 created at a junction of the first slot wall 114 and the first rounded end face 108 and a second apex 124 created at a junction of the second slot wall 116 and the second rounded end face 110. The first and second apexes 124 are positioned in contact with the circuit board 56 with one of the light emitting diodes 58 positioned within the slot 112. According to other embodiments, the apexes 124 can be positioned proximate to, but not in direct contact with the circuit board 56.

Figure 15:
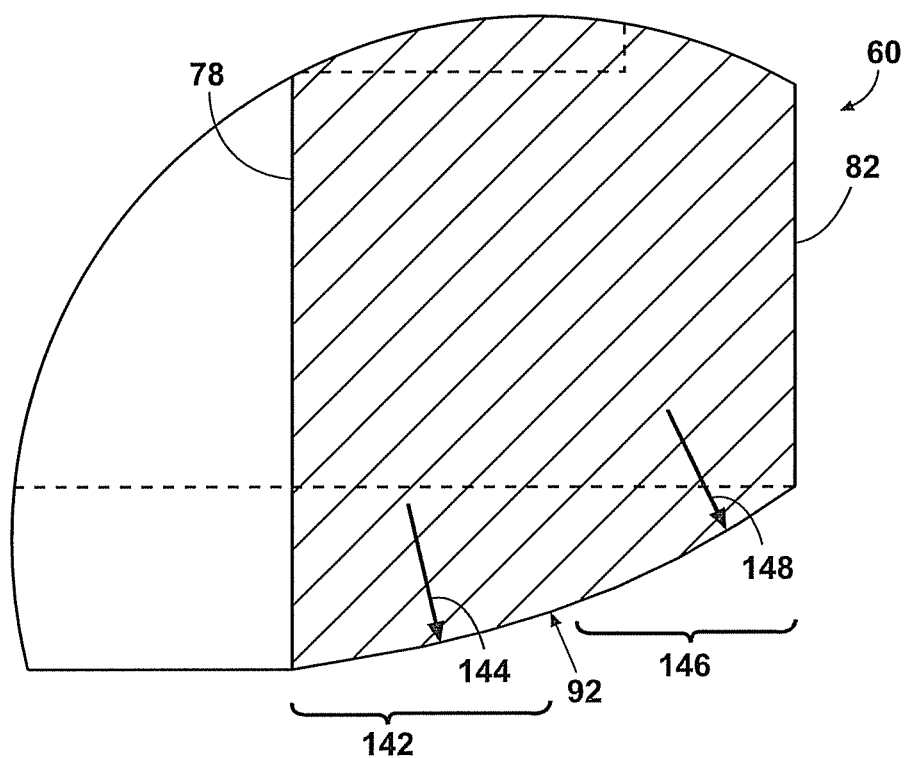
FIG. 15 is a cross sectional elevational view of surface 92 of FIG. 8.

Referring to FIG. 15, curved upper surface 92 according to several embodiments can be defined by two or more individual curved surface portions. In the exemplary embodiment shown, a first curve portion 142 has a first radius of curvature 144 and a second curve portion 146 has a second radius of curvature 148. First and second radius of curvatures 144, 148 can be equal or different from each other. The difference in curvature between the first and second curve portion 142, 146 can be optimized to maximize the focal length of the light transmitted through light pipe unit 60 to a distance selected by the manufacturer.

Light pipe units 60 of the present disclosure provide several advantages. By creating the slot 112 between first and second slot walls 112, 114, the light pipe unit 60 can be positioned to provide transparent material in contact with, or in close proximity to the exposed surfaces of the LEDs 58. This permits a greater amount of light from the LEDs 58 to be captured and transmitted via the light pipe unit 60. By creating apexes where the first and second slot walls 112, 114 meet the curved end surfaces 108, 110, contact between the light pipe unit 60 and the circuit board can be minimized. The curved end surfaces 108, 110 also promote reflection of light emitted from the LEDs 58 that is not parallel or co-axial with the raised portions 103 to be redirected outwardly from the light pipe unit 60, increasing the total light emission. Using two or more curve portions 142, 146 each having a different radius of curvature further promotes transmission of reflected light from the LEDs 58. By sizing the raised portions 103 to slidably or frictionally fit against the walls defined within the curved bores 128 of the light pipe cap 62, these spaces or gaps can be minimized or eliminated, eliminating the need for a moisture or dirt sealant in these spaces.

Figure 16:
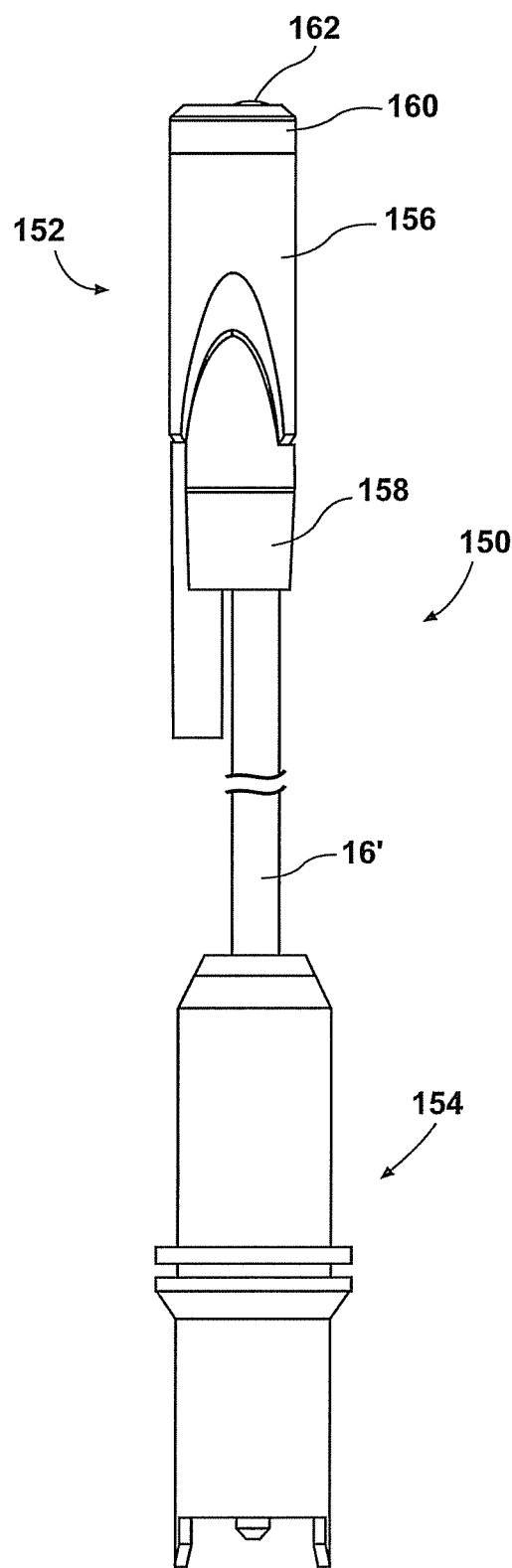
FIG. 16 is a front elevational view of an imager assembly according to a further embodiment of the present disclosure.

Referring to FIG. 16, according to additional embodiments of the present disclosure, an imager assembly 150 can include an imager head sub-assembly 152 which is flexibly connected to a housing connection sub-assembly 154 using a flexible tube 16'. Imager head sub-assembly 152 includes an imager body 156 which is connected to the flexible tube 16' using a connection ferrule 158. An imager end cap 160 is threadably connected at an opposite end of imager body 156 with respect to the connection ferrule 158, and a tapered light pipe 162 is retained in the imager end cap 160.

Figure 17:
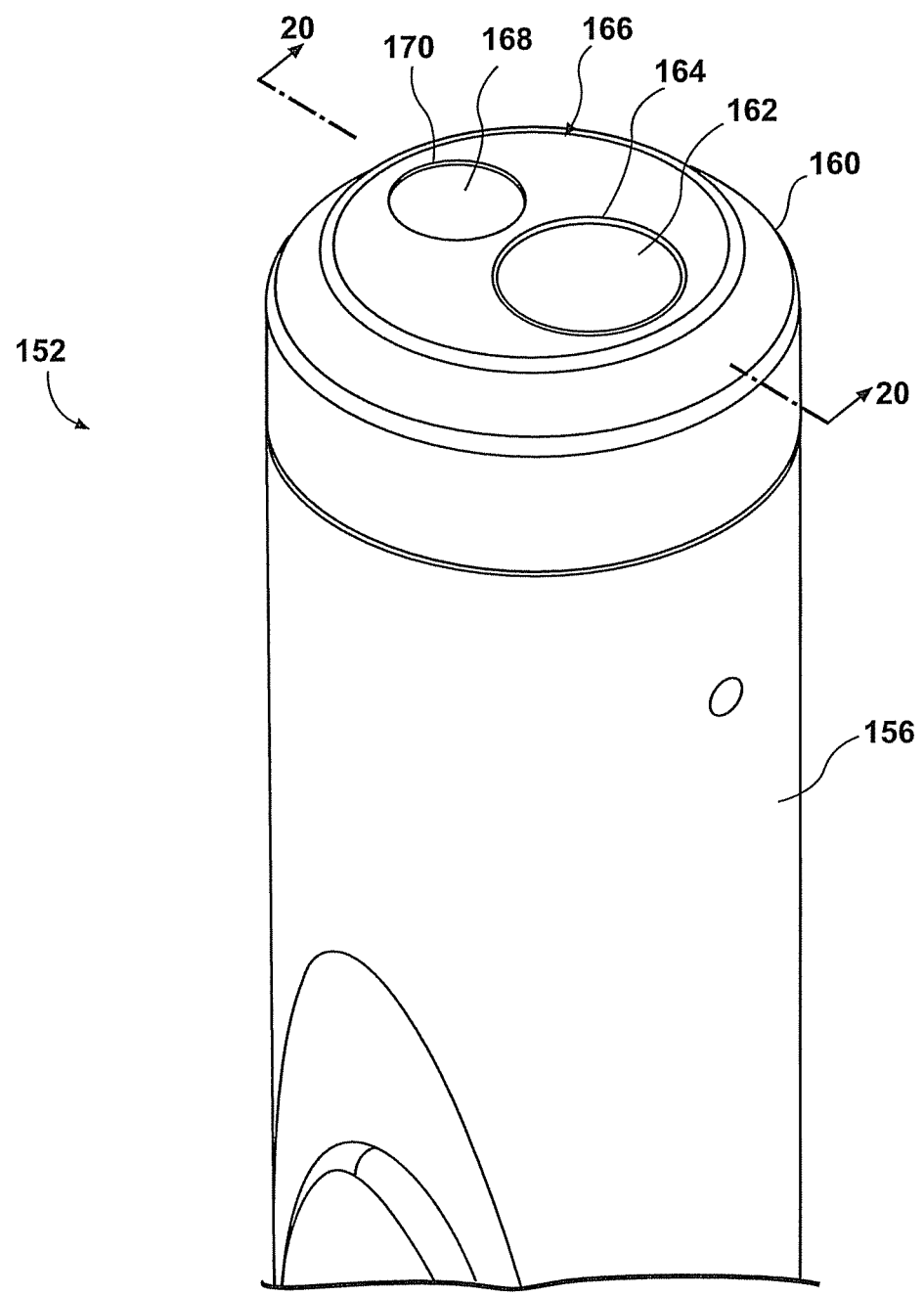
FIG. 17 is a front elevational view of an imager head of the imager assembly of FIG. 16.

Referring to FIG. 17, further features of imager head sub-assembly 152 include a light pipe mounting cavity 164 adapted to receive the tapered light pipe 162. Light pipe mounting cavity 164 is created in a raised portion 166 of imager end cap 160. Additionally, a lens 168 such as a sapphire lens is also retained in imager end cap 160 in a lens mounting cavity 170. Similar to previous embodiments, light emitted through tapered light pipe 162 and reflected off a remote object (not shown) is received in lens 168.

Figure 18:
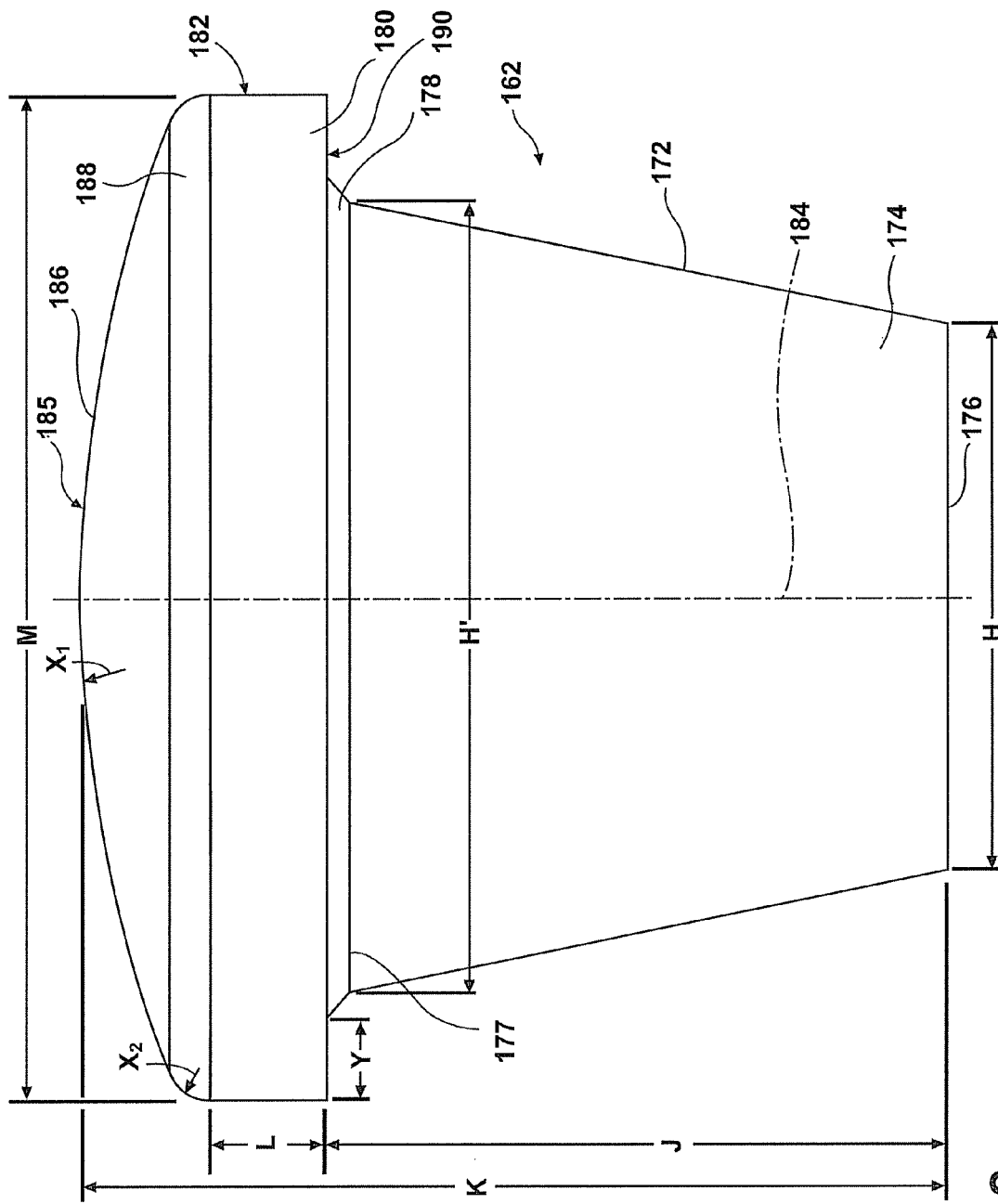
FIG. 18 is a front elevational view of a tapered light pipe of the imager assembly of FIG. 16.

Referring to FIG. 18, tapered light pipe 162 defines a homogeneous molded polymeric material part which can be made using a material such as a transparent acrylic plastic. Tapered light pipe 162 includes a conical shaped perimeter wall 172 defining a light pipe body 174 extending from a first body end 176 which has a minimum body diameter "H" to a second body end or body junction 177 which has a maximum body diameter "H'". From the second body end or body junction 177, a transition portion 178 can extend oppositely with respect to first body end 176 and can be formed as shown having a conical shape or can also be formed having a radius at the discretion of the designer. Transition portion 178 homogeneously connects to a flange portion 180. Flange portion 180 extends outwardly with respect to a light pipe longitudinal axis 184 to a flange perimeter wall 182. According to several embodiments, flange portion 180 is generally oriented transversely with respect to light pipe longitudinal axis 184 and flange perimeter wall 182 is oriented parallel to light pipe longitudinal axis 184.

According to several embodiments, a convex curved surface 185 includes first and second arc portions 186, 188, the first arc portion 186 having a radius of curvature $X_1$ larger than a radius of curvature $X_2$ of the second arc portion 188. The second arc portion 188 tangentially meets the flange perimeter wall 182 of flange portion 180. Convex curved surface 185 connects opposed faces of flange perimeter wall 182 and extends oppositely (upwardly as viewed in FIG. 18) with respect to first body end 176. Second arc portion 188 smoothly transitions into first arc portion 186. First arc portion 186 at its intersection with longitudinal axis 184 and measured from first body end 176 defines a total height "K" of tapered light pipe 162. Flange perimeter wall 182 has a flange thickness "L". Flange portion 180 extends radially outward from either or both body junction 177 and transition portion 178 to define a flange mount surface 190 which faces in a similar direction to first body end 176. Flange mount surface 190 is substantially planar, is oriented transverse to light pipe longitudinal axis 184, and extends from a furthest outward extension of either transition portion 178 or the body second end (at body junction 177) by an extension dimension "Y". According to several embodiments flange portion 180 is circular having a flange diameter "M". Flange diameter "M" is larger than second end maximum diameter "H'" to create flange mount surface 190. According to further embodiments, flange perimeter wall 182 can also define additional geometric shapes including but not limited to oval, rectilinear, and multi-facetted, with the geometry of convex curved surface 185 adjusted accordingly.

Figure 19:
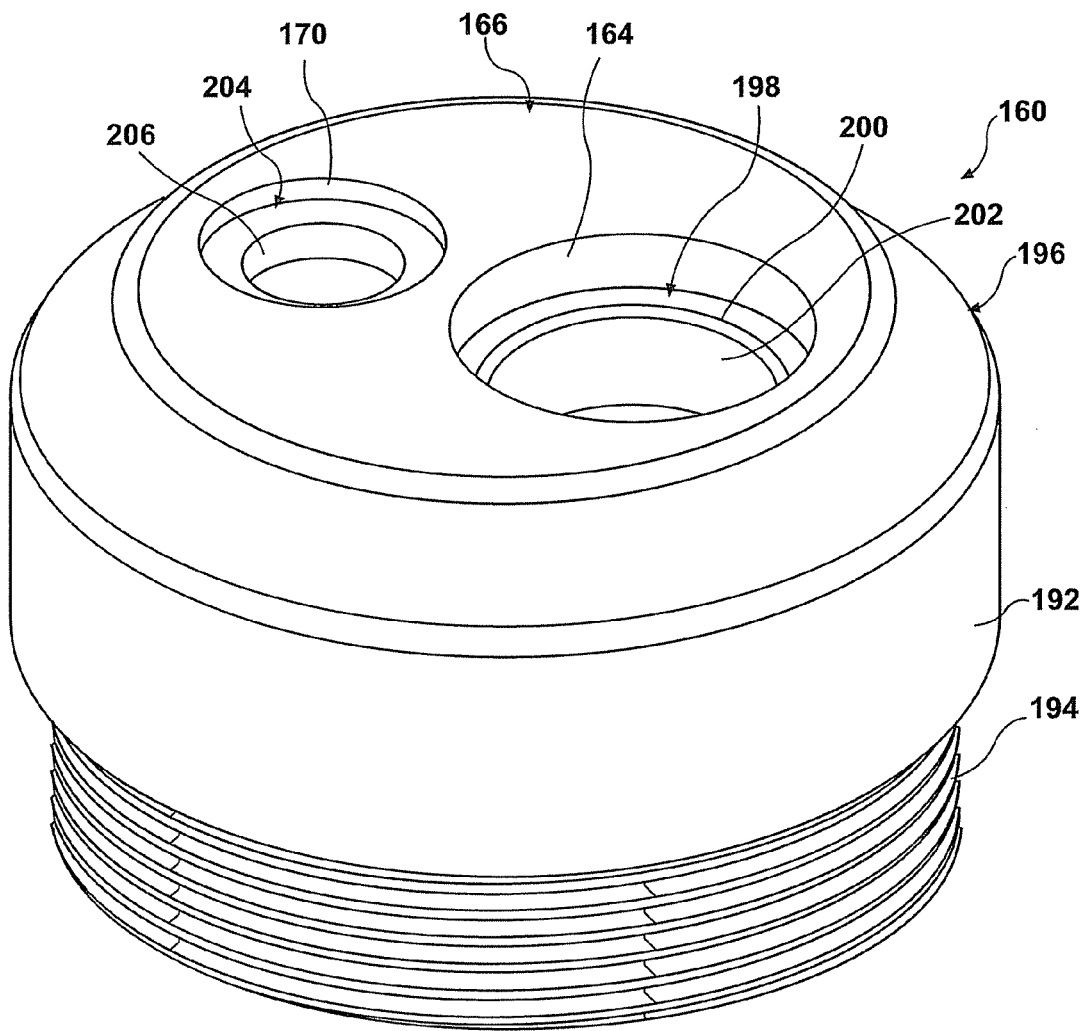
FIG. 19 is a front perspective view of an imager end cap for the image assembly of FIG. 16.

Referring to FIG. 19 and again to FIG. 18, imager end cap 160 includes a cap body 192 which is substantially circular in shape having a threaded body portion 194 extending axially with respect to cap body 192. An arc shaped surface 196 extends inwardly from the perimeter wall of cap body 192 and has raised portion 166 extending outwardly therefrom. Light pipe mounting cavity 164 can further include a counterbore seating surface 198 which is adapted to receive flange mount surface 190 of tapered light pipe 162 which will be shown and described in greater detail in reference to FIGS. 20 and 21. Inwardly directed from counterbore seating surface 198 is a chamfer 200 which transitions into a through bore 202. Lens mounting cavity 170 is similarly configured, having a counterbore seating surface 204 and a through bore 206 centrally disposed with respect to counterbore seating surface 204.

Figure 20:
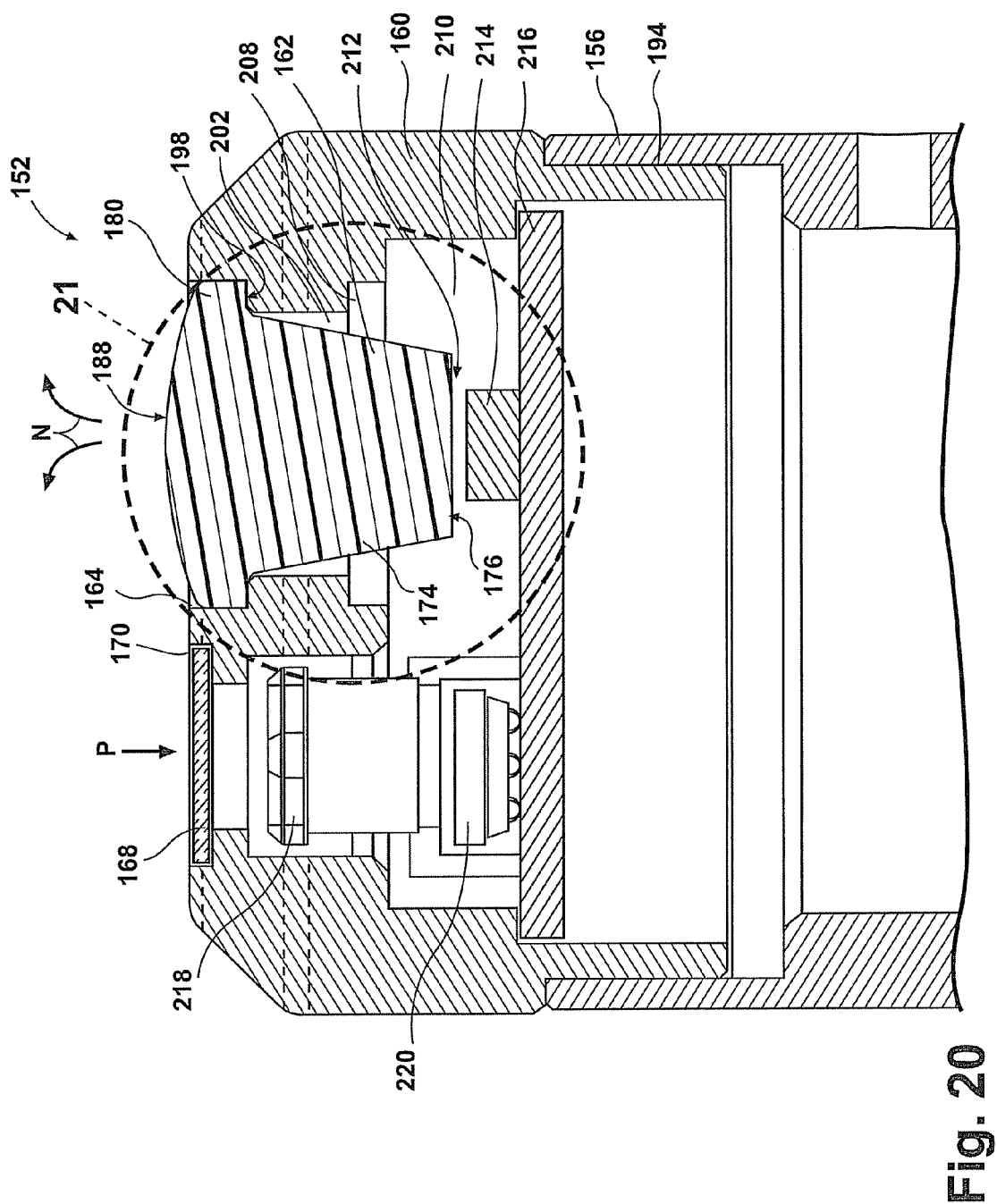
FIG. 20 is a cross sectional front elevational view taken at section 20 of Figure.
Figure 21:
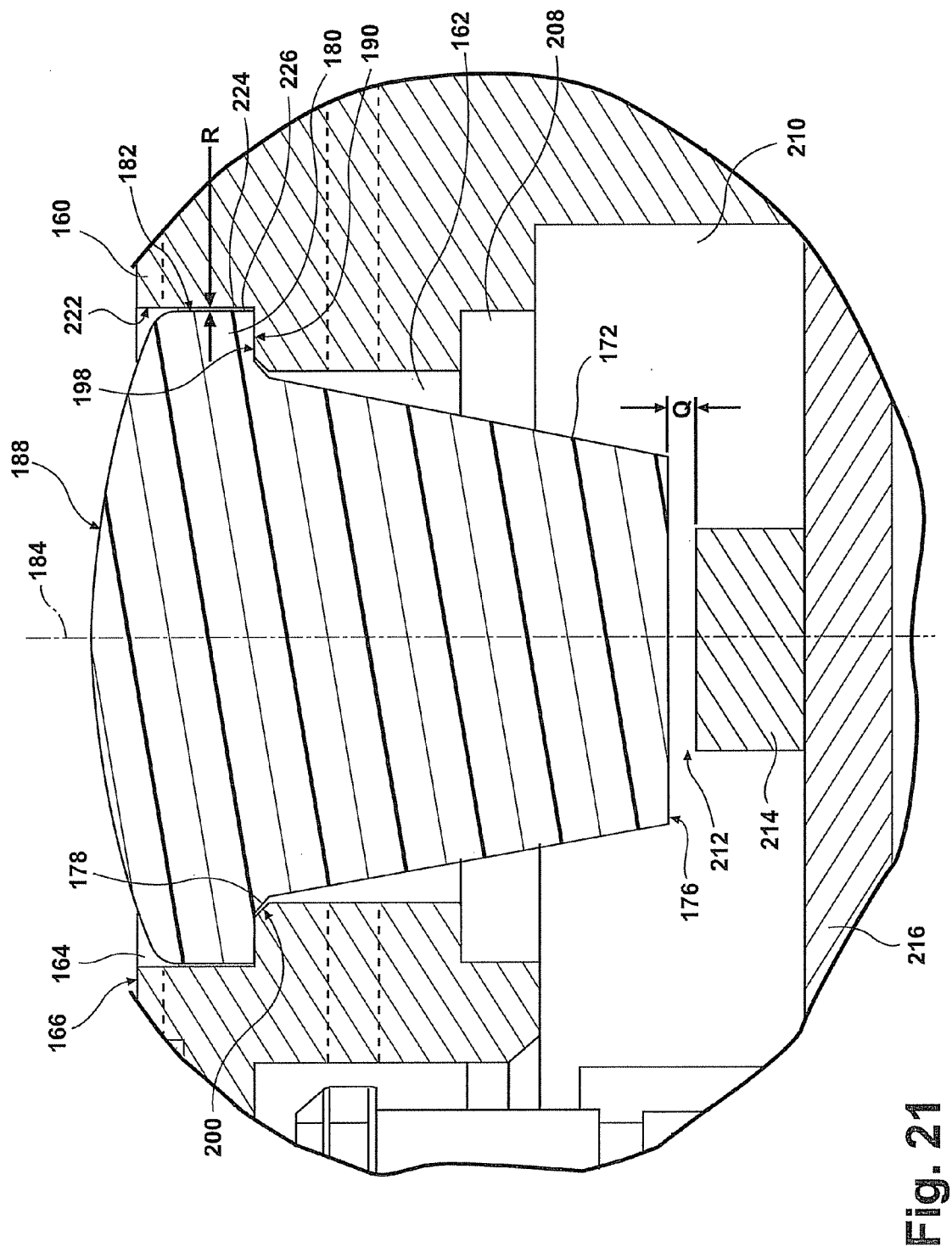
FIG. 21 is a cross sectional front elevational view taken at area 21 of FIG. 20.

Referring to FIG. 20, tapered light pipe 162 is shown during installation into imager end cap 160 with respect to further components of imager head sub-assembly 152. The flange portion 180 of tapered light pipe 162 is shown positioned partially within the light pipe mounting cavity 164 just prior to contact between flange portion 180 and counterbore seating surface 198. Light pipe body 174 is freely positioned within through-bore 202 and additionally freely positioned within a recessed cavity 208 and a clearance cavity 210 also created within imager end cap 160. No portion of light pipe body 174 contacts any feature of imager end cap 160. A clearance gap 212 is also maintained when tapered light pipe 162 is fully seated with respect to counterbore seating surface 198 such that there is no physical contact between first body end 176 of tapered light pipe 162 and a light emitting diode (LED) 214 which is connected to a circuit board 216.

Light emitted by LED 214 is transmitted through clearance gap 212 and into first body end 176 to be emitted in a plurality of dispersion paths "N" via convex curved surface 185. The clearance gap 212 is fixed when threaded body portion 194 of imager end cap 160 is fully threadably engaged with imager body 156, thereby also fixing a position of circuit board 216 with respect to both imager end cap 160 and imager body 156. In addition to positioning tapered light pipe 162 in light pipe mounting cavity 164, lens 168 is also fixed within lens mounting cavity 170 such that reflected light received in a receiving path "P" through lens 168 is directed through a lens assembly 218 to be received by an imager device 220 also fixedly connected to circuit board 216.

Referring to FIG. 21 and again to FIG. 16, tapered light pipe 162 is shown in a fully seated position with respect to imager end cap 160 and LED 214. The installed or fully seated position of tapered light pipe 162 is reached when flange mount surface 190 physically contacts counterbore seating surface 198. According to several embodiments, the only direct physical contact between tapered light pipe 162 and imager end cap 160 and/or imager head sub-assembly 152 occurs at the surface contact between flange mount surface 190 and counterbore seating surface 198. This minimizes the potential paths for light transmitted through tapered light pipe 162 diffracting into and reflecting off the interior surfaces of imager end cap 160. When tapered light pipe 162 is in the fully seated position, a clearance gap "R" is maintained between a cavity wall 222 of light pipe mounting cavity 164 and flange perimeter wall 182, defining a separation space 224. An adhesive 226 is applied to fill the separation space 224, using only a minimum amount of adhesive 226 to fill the separation space 224 without the adhesive 226 contacting any other portion of tapered light pipe 162.

It is further noted that chamfer 200 of imager end cap 160 defines a different angle with respect to light pipe longitudinal axis 184 than an angle defined by transition portion 178 with respect to longitudinal axis 184, so that no contact occurs between transition portion 178 and chamfer 200. A gap spacing dimension "Q" defined by the clearance gap 212 between first body end 176 and LED 214 is maintained in the seated position of tapered light pipe 162. Gap spacing dimension "Q" is maintained as a positive value such that clearance between first body end 176 of tapered light pipe 162 and LED 214 is always provided. It is further noted that light pipe longitudinal axis 184 is substantially coaxially aligned with a longitudinal axis of LED 214 to maximize the light admitted by LED 214 being transmitted through tapered light pipe 162. Light which is reflected within recessed cavity 208 and clearance cavity 210 can also enter tapered light pipe 162 through conical shaped perimeter wall 172.

Tapered light pipes of the present disclosure offer several advantages. These include the use of a flange portion extending radially outward with respect to a conical shaped perimeter wall, which permits the tapered light pipe 162 to be mounted at the flange portion, minimizing the amount of light reflection within the imager end cap 160. Also, by maintaining clearance gap "R" between flange perimeter wall 182 and cavity wall 222, the use of adhesive 226 to fill the clearance gap "R" defines the only required sealing point between tapered light pipe 162 and imager end cap 160. Adhesive 226 is applied at a position which also environmentally seals the components within imager head sub-assembly 152 from moisture and dirt, and does not impact light transmission through tapered light pipe 162. By further controlling an angle of conical perimeter wall 172 with respect to light pipe longitudinal axis 184, and the amount of curvature of convex curved surface 185, the light dispersion angle for tapered light pipe 162 can be modified at the discretion of the designer. Further, by maintaining the orientation of flange mount surface 190 substantially perpendicular with respect to light pipe longitudinal axis 184, and orienting the counterbore seating surface 198 of imager end cap 160 also substantially transverse with respect to light pipe longitudinal axis 184, co-axial orientation of tapered light pipe 162 and LED 214 can be provided.

According to further embodiments, transition portion 178 can also be formed as a radius at the discretion of the designer to suit a mold used to create tapered light pipe 162. Transition portion 178 can also be eliminated entirely, having body junction 177 in direct contact with flange portion 180. The geometry or use of chamfer 200 can therefore also be modified, or chamfer 200 can also be eliminated at the discretion of the designer.

The term "homogeneous(ly)" as used herein is defined as a part, component, member, or the like (collectively the part) having all portions and/or connections of the part formed of the same material and by the same process used to create the part, such as by molding including injection molding, or casting, such that no portion(s) or connections of the part require connection to any other portion by a secondary process including but not limited to welding, adhesive bonding, mechanical connection, second molding or casting process, or the like, and the chemical properties of the part material are substantially equivalent throughout the part.

What is claimed is:

1. A light pipe assembly for a video imaging device, comprising:
   a tapered light pipe comprising a homogeneous one-piece body of a transparent polymeric material being configured to transmit light through the transparent polymeric material of the homogeneous one-piece body, the body including:
      a first end defining a minimum body diameter oppositely positioned with respect to a second end defining a maximum body diameter; and
      a conical shaped perimeter wall extending between the first and second ends;
   a flange portion homogeneously connected to the body at the second end and extending transversely with respect to a longitudinal axis of the light pipe, a flange diameter of the flange portion being greater than the maximum body diameter; and a light emitting device being aligned with the homogeneous one-piece tapered light pipe and operable to emit light through the homogeneous one-piece tapered light pipe.

2. The light pipe assembly of claim 1, wherein the homogeneous one-piece body further includes a convex curved surface axially extending outward from the flange portion and oppositely directed with respect to the first end, the convex curved surface homogeneously connected to the flange portion and tangentially meeting a flange perimeter wall of the flange portion.

3. The light pipe assembly of claim 2, further including a flange mount surface of the flange portion extending radially outwardly from the second end of the homogeneous one-piece body, facing oppositely with respect to the convex curved surface, and oriented transverse to the longitudinal axis.

4. The light pipe assembly of claim 3, wherein the flange perimeter wall is oriented parallel to the longitudinal axis and perpendicular to the flange mount surface.

5. The light pipe assembly of claim 2, wherein the convex curved surface comprises first and second arc portions, the first arc portion having a radius of curvature larger than a radius of curvature of the second arc portion, the second arc portion tangentially meeting the flange perimeter wall of the flange portion, the second arc portion smoothly transitioning into the first arc portion.

6. The light pipe assembly of claim 1, further including: a body junction at the maximum diameter second end of the homogeneous one-piece body; and a transition portion homogeneously connecting the body junction at the second end to the flange portion, the transition portion extending outward toward the flange portion.

7. The light pipe assembly of claim 1, wherein the homogeneous one-piece body, the flange portion, and a convex curved surface are homogeneously connected and created from a transparent polymeric material.

8. The light pipe assembly of claim 1, wherein the homogeneous one-piece body increases in diameter from the first end to the second end, the first end being configured to receive the light and transmit the light through the transparent polymeric material to the second end being configured to emit the light.

9. The light pipe assembly of claim 1, further comprising an imager end cap having a light pipe mounting cavity including a counterbore seating surface.

10. An imager assembly for a video imaging device, comprising:
a light pipe, the light pipe comprising a homogeneous one-piece tapered light pipe of a transparent polymeric material being configured to transmit light through the transparent polymeric material of the homogeneous one-piece tapered light pipe, including:
a body, the body comprising a conical shaped body including a first end having a minimum body diameter and an oppositely positioned second end having a maximum body diameter;
a flange portion homogeneously connected to the body second end and extending transversely with respect to a longitudinal axis of the homogeneous one-piece tapered light pipe, a flange diameter of the flange portion being greater than the maximum body diameter; and a convex curved surface axially extending from the flange portion and oppositely directed with respect to the body, the convex curved surface including first and second arc portions having the second arc portion smoothly transitioning into the first arc portion;

an imager end cap having a light pipe mounting cavity including a counterbore seating surface; and a flange mount surface of the flange portion oriented transverse to the longitudinal axis, the flange mount surface contacting the counterbore seating surface in a seated position of the homogeneous one-piece tapered light pipe, contact between the flange mount surface and the counterbore seating surface defining the only portion of the homogeneous one-piece tapered light pipe in contact with the imager assembly.

11. The imager assembly of claim 10, further comprising: an imager body connected to the imager end cap; and a circuit board contacted by the imager end cap in the seated position of the tapered light pipe.

12. The imager assembly of claim 11, further comprising a light emitting diode connected to the circuit board and axially oriented with respect to the longitudinal axis of the homogeneous one-piece tapered light pipe, the light emitting diode being spaced from the first end of the homogeneous one-piece tapered light pipe creating a gap spacing when the homogeneous one-piece tapered light pipe is in the seated position.

13. The imager assembly of claim 10, further comprising:
a cavity wall of the light pipe mounting cavity oriented transverse to the longitudinal axis of the homogeneous one-piece tapered light pipe when the homogeneous one-piece tapered light pipe is positioned in the seated position; and
a flange perimeter wall of the flange portion oriented transverse to the longitudinal axis of the homogeneous one-piece tapered light pipe;
wherein the homogeneous one-piece tapered light pipe in the seated position has the flange perimeter wall spaced from the cavity wall by a clearance gap such that the flange perimeter wall does not directly contact the cavity wall.

14. The imager assembly of claim 13, further comprising an adhesive applied within the clearance gap, the adhesive contacting only the flange perimeter wall and the cavity wall to adhesively retain the homogeneous one-piece tapered light pipe in the light pipe mounting cavity and to create an environmental seal between the homogeneous one-piece tapered light pipe and an internal cavity of the imager end cap.

15. The imager assembly of claim 10, wherein the homogeneous one-piece tapered light pipe further includes:
a conical shaped perimeter wall extending between the first and second ends; and
a body junction defined at the maximum diameter second end of the body.

16. The imager assembly of claim 10, wherein the homogeneous one-piece tapered light pipe further includes a transition portion homogeneously connecting the body junction at the second end to the flange portion, the transition portion extending outward toward the flange portion.

17. The imager assembly of claim 10, wherein the flange mount surface and the counterbore seating surface contact the homogeneous one-piece tapered light pipe limiting the paths for light transmitted through the transparent polymeric material of the homogeneous one-piece light pipe.

18. An imager assembly for a video imaging device, comprising:
a light pipe, the light pipe comprising a homogeneous one-piece tapered light pipe of a transparent polymeric material being configured to transmit light through the transparent polymeric material of the homogeneous one-piece tapered light pipe such that light is transmissible in a direct path defined through the light pipe, including:
  a body including a first end having a minimum body diameter and an oppositely positioned second end having a maximum body diameter, and a conical shaped perimeter wall extending between the first and second ends; and
  a flange portion homogeneously connected to the body second end and extending transversely with respect to a longitudinal axis of the homogeneous one-piece tapered light pipe, a flange diameter of the flange portion being greater than the maximum body diameter;
an imager end cap having a light pipe mounting cavity including a counterbore seating surface having the flange portion contacting the counterbore seating surface;
a circuit board having a light emitting diode connected to the circuit board emitting light through the homogeneous one-piece tapered light pipe; and
an imager body, the imager end cap connected to the imager body aligning the light emitting diode with the homogeneous one-piece tapered light pipe.

19. The imager assembly of claim 18, wherein the homogeneous one-piece tapered light pipe further includes a convex curved surface axially extending from the flange portion and oppositely directed with respect to the body.

20. The imager assembly of claim 18, further including a planar flange mount surface of the flange portion oriented transverse to the longitudinal axis, wherein the flange portion contacts the counterbore seating surface at the flange mount surface in a seated position of the homogeneous one-piece tapered light pipe, contact between the flange mount surface and the counterbore seating surface defining the only portion of the homogeneous one-piece tapered light pipe in direct contact with the imager assembly.

21. An imaging device, comprising:
  an imager body;
  an imager end cap having a light pipe mounting cavity including a counterbore seating surface and a cavity wall oriented transverse to the counterbore seating surface, the imager end cap connected to the imager body;
  a light pipe, the light pipe comprising a homogeneous one-piece tapered light pipe of a transparent polymeric material being configured to transmit light through the transparent polymeric material of the homogeneous one-piece tapered light pipe such that light is transmissible in a direct path defined through the light pipe, the light pipe including:
    a body including a first end having a minimum body diameter and an oppositely positioned second end having a maximum body diameter, and a conical shaped perimeter wall extending between the first and second ends;
    a flange portion homogeneously connected to the body second end having a planar flange mount surface extending transversely with respect to a longitudinal axis of the homogeneous one-piece tapered light pipe, a flange diameter of the flange portion being greater than the maximum body diameter, the flange mount surface contacting the counterbore seating surface defining a seated position of the homogeneous one-piece tapered light pipe, contact between the flange mount surface and the counterbore seating surface defining the only portion of the homogeneous one-piece tapered light pipe in direct contact with the imager assembly; and
    a flange perimeter wall of the flange portion being spaced from the cavity wall in the seated position, defining a clearance gap; and
  an adhesive applied only within the clearance gap to fix the flange perimeter wall to the cavity wall.

22. The imaging device of claim 21, further comprising:
  a circuit board retained between the imager end cap and the imager body; and
  a light emitting diode connected to the circuit board emitting light through the homogeneous one-piece tapered light pipe.

23. The imaging device of claim 22, further comprising: a flexible tube connected to the imager body; and a display housing connected to the flexible tube opposite to the imager body, the display housing having a video image view screen adapted to display an image illuminated by the light emitted by the light emitting diode digitally transmitted from the circuit board through a wiring harness.

* * * * *